United States Patent [19]

Strand

[11] Patent Number: 4,795,516

[45] Date of Patent: Jan. 3, 1989

[54] METHOD OF CONTINUOUS PRODUCTION OF A BIOMEDICAL ELECTRODE

[75] Inventor: Jerome E. Strand, Hudson, Wis.

[73] Assignee: Minnesota Mining and Manufacturing Company, St. Paul, Minn.

[21] Appl. No.: 69,490

[22] Filed: Jul. 2, 1987

Related U.S. Application Data

[62] Division of Ser. No. 865,521, May 21, 1986, Pat. No. 4,694,835.

[51] Int. Cl.[4] .................. A61B 5/04; B32B 31/06; B32B 31/18
[52] U.S. Cl. ..................... 156/235; 29/877; 156/238; 156/265; 156/268; 156/301
[58] Field of Search .................. 128/639–641, 128/798, 802, 803; 29/877, 876; 156/230, 235, 238, 241, 265, 247, 299–302, 268

[56] References Cited

U.S. PATENT DOCUMENTS

| | | | |
|---|---|---|---|
| 3,774,592 | 11/1973 | Lahr | 128/2.1 E |
| 4,166,465 | 9/1979 | Esty | 128/303.13 |
| 4,257,424 | 3/1981 | Cartmell | 128/641 |
| 4,370,984 | 2/1983 | Cartmell | 125/640 |
| 4,393,584 | 7/1983 | Bare et al. | 29/877 |
| 4,524,087 | 6/1985 | Engel | 427/2 |
| 4,539,996 | 9/1985 | Engel | 128/640 |
| 4,635,642 | 1/1987 | Cartmell et al. | 128/639 |

FOREIGN PATENT DOCUMENTS

| | | |
|---|---|---|
| 0142372 | 5/1985 | European Pat. Off. ........... 128/641 |
| 84307882.5 | 5/1985 | European Pat. Off. . |
| 2159717A | 12/1985 | United Kingdom . |
| WO81/02097 | 8/1981 | World Int. Prop. O. . |

Primary Examiner—Michael W. Ball
Assistant Examiner—Jeff H. Aftergut
Attorney, Agent, or Firm—Donald M. Sell; Dale E. Hulse

[57] ABSTRACT

A biomedical electrode comprising a backing, a biocompatible pressure sensitive adhesive (PSA), a bonding sheet, an electrical conductor, and an electrolyte composition is shown. The biocompatible PSA coats one surface of the backing. The bonding sheet has first and second faces smaller in surface area then the backing. The first face is bonded to the biocompatible PSA. The electrical conductor has a top face with first and second surfaces. The first surface spans a portion of the bonding sheet and the second surface adheres to the biocompatible PSA. The electrical conductor has a bottom face with a third surface opposing the first surface and a fourth surface opposing the second surface. In electrical contact with the third surface is the electrolyte composition. The electrolyte composition is also, adhered to a portion of bonding sheet. A continuous high speed and low cost method of manufacture is also shown.

4 Claims, 3 Drawing Sheets

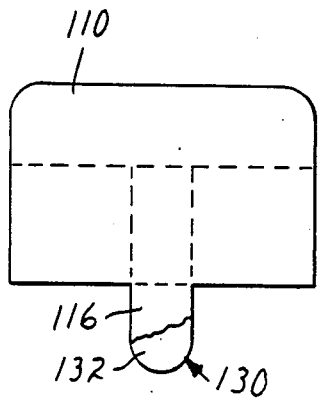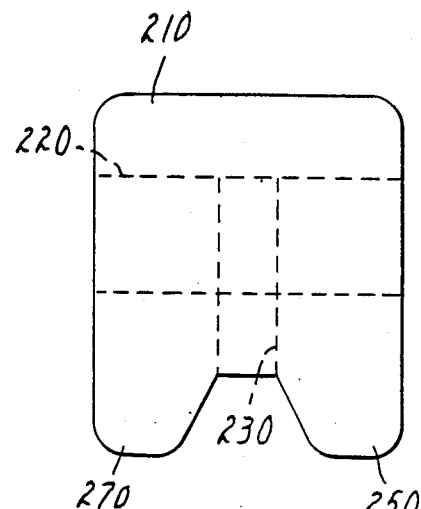

METHOD OF CONTINUOUS PRODUCTION OF A BIOMEDICAL ELECTRODE

This is a division of application Ser. No. 865,521, filed May 21, 1986, now U.S. Pat. No. 4,694,835.

FIELD OF THE INVENTION

This invention relates to electrodes useful in detecting the electrical currents generated by biomedical events. This invention also relates to a method of manufacturing such electrodes.

BACKGROUND OF THE INVENTION

Biomedical electrodes are used with electrocardiograph ("ECG/EKG") instruments to trace and monitor the electric potentials associated with electric currents that transverse the heart in resting diagnostic procedures, in surgical and emergency room procedures, in cardiac and critical care units in ambulatory monitoring, and in stress diagnostic procedures. The electrodes need to accurately detect and transmit electrical signals produced by biomedical events. Generally this need has required use of relatively large (and therefore) expensive electrical conductors. Electrolyte compositions such as conductive adhesives and conductive gels are used to reduce the size of the electrical conductor. These electrodes also need to stay in place with electrical contact between the skin and the electrode. This requirement can be a problem with all biomedical electrodes and is a particular problem in any circumstance where the electrode stays in place for a long period of time and the patient moves or is moved during monitoring.

U.S. Pat. No. 4,524,087 to Engel discloses a grounding plate biomedical electrode wherein the electrical conductor or "plate" is a polyester film coated on one side with a conductive metal. The conductive metal surface of the plate is coated with an electrically conductive pressure-sensitive adhesive. Overlying the polyester film side of the plate and extending outward from its periphery is an adhesive coated backing to secure the electrode to the skin of a patient. The electrode has a connector tab to electrically connect the electrode to a lead wire. An insulating strip is placed transversely to the connector tab on the exposed surface of the conductive adhesive.

A sensing electrode sold under the brand name Littmann ® Diagnostic EKG Electrode (3M Co., St. Paul, Minn.) includes a film of polymeric material coated on one side with tin. A single, continuous layer of an electrically-conductive pressure-sensitive adhesive covers approximately three quarters of the tin surface while one quarter of the tin surface is a strip along one edge and free for attachment to the lead-wire of an electrical sensing device. The electrically-conductive pressure-sensitive adhesive of the Littmann$^R$ sensing electrode, while adequately conducting electrical current, does not always provide sufficient adhesion to the skin over long periods, e.g., days of ECG/EKG monitoring.

U.S. Pat. No. 4,166,465 to Esty discloses a grounding plate biomedical dispersive electrode with a backing dimensioned to be generally rectangular and provided with bifurcated ends or wings which form a generally broad notch or recessed portion between each of the bifurcated ends. Positioned between the two "wings" is a tab to which a lead-wire connector is attached.

EPO Application Ser. No. 84 307 882.5 (published May 22, 1985) discloses a biomedical electrode having a terminal member, a retainer sheet, an ionically conductive layer, and a medical tape. The terminal member has a base with upper and lower surfaces and a post integral with the base for connection to a lead wire of an electromedical instrument. The retainer sheet and medical tape each have an aperture to receive and surround the terminal post. The retainer sheet overlies the terminal base and the medical tape overlays the retainer sheet. The ionically conductive layer contacts the lower surface by the terminal base and extends peripherally beyond the lower surface of the base to contact the retainer sheet. A metal or metallized layer may be included between the retainer sheet and the upper surface of the base and the retainer sheet and the ionically conductive layer. The retainer sheet and metal or metallized layer are shown with the same surface area and shape and aligned when assembled. The ionically conductive layer is shown with a perimeter equal to that of the retainer sheet and metal or metallized layer. It is assembled with its peripheral edges aligned with those of the retainer sheet and metal or metallized layer. The medical tape has a surface area larger than those of the retainer sheet, the metal or metallized layer and the ionically conductive layer. It extends peripherally beyond the ionically conductive layer to aid in securing the electrode to skin.

SUMMARY OF THE INVENTION

One aspect of this invention is a biomedical electrode comprising a backing, a biocompatible pressure sensitive adhesive (PSA), a bonding sheet, an electrical conductor, and an electrolyte composition. The biocompatible PSA coats one surface of the backing. The bonding sheet has first and second faces smaller in surface area than the backing. The first face is bonded to the biocompatible PSA. The electrical conductor has top and bottom faces. The top face is divided into first and second surfaces, and the bottom face is divided into a third surface opposing the first surface and a fourth surface opposing the second surface. The first surface spans a portion of the second face of the bonding sheet and the second surface is adhered to a portion of the biocompatible PSA. The electrolyte composition may be any electrically conductive gel or preferably is an electrically-conductive pressure sensitive adhesive (PSA). The electrolyte composition has a surface area smaller than that of the backing. This electrolyte composition is (1) in electrical contact with the third surface of the electrical conductor, and (2) adhered to at least a portion of the second face of the bonding sheet which is not spanned by the electrical conductor.

In a preferred embodiment, the biomedical PSA coats an entire surface of the backing and the backing/biocompatible PSA have cutouts along one side so that the side with the cutouts has three tabs. In this embodiment, the second surface of the electrical conductor is bonded to the biocompatible PSA along the middle tab and serves to connect the electrode to a lead-wire. The other two tabs serve to reinforce the electrode and prevent dislodgment when force is applied to the middle tab.

In another preferred embodiment the electrical conductor is a film coated on at least its bottom face with a conductive metal and conductive metal salt. The preferred conductive metal is silver while the preferred conductive metal is silver chloride. When the total silver, silver ion content does not exceed 15 g/m$^2$, the electrode of the present invention is X-Ray transluscent and almost not visible in X-Rays.

Another aspect of this invention is a method of manufacturing disposable biomedical electrodes. A web of backing having a coating of biocompatible PSA on one surface is provided. A bonding sheet web narrower than the backing web is continuously laminated to the biocompatible PSA coated surface of the backing web. A plurality of electrical conductors are placed at predetermined transverse locations along the length of the backing and bonding sheet webs such that a first surface of the electrical conductors contacts the bonding sheet web and a second surface adheres to the biocompatible PSA on the backing web. A web of carrier sheet bearing a continuous strip of an electrolyte composition which strip is aligned with the bonding sheet web is continuously laminated to the composite. The strip overlaps at least a portion of each of the electrical conductors and contacts the bonding sheet web. The carrier sheet is delaminated, a release liner is laminated and individual electrodes are cut from the web.

The electrode of the present invention uses inexpensive materials to yield a product that performs as well as currently available electrodes. Biocompatible adhesives tend to be hydrophobic. Known electrolyte compositions (conductive gels and conductive adhesives) are very hydrophyllic and do not always adhere well to known biocompatible adhesives. The present construction allows both to be used. Additionally, the present construction stays in place. It also has a flat profile making it easier to package and more comfortable in use. As noted above, when the silver, silver ion content is no greater than 15 grams per square meter, the electrode is X-Ray transluscent. The method of manufacture is adaptable for continuous high speed and low cost manufacture.

BRIEF DESCRIPTION OF THE DRAWINGS

FIG. 3 is a view of a second embodiment of the biomedical electrode of this invention.

FIG. 4 is a view of a third embodiment of the biomedical electrode of this invention.

DETAILED DESCRIPTION OF THE INVENTION

Figure 1:
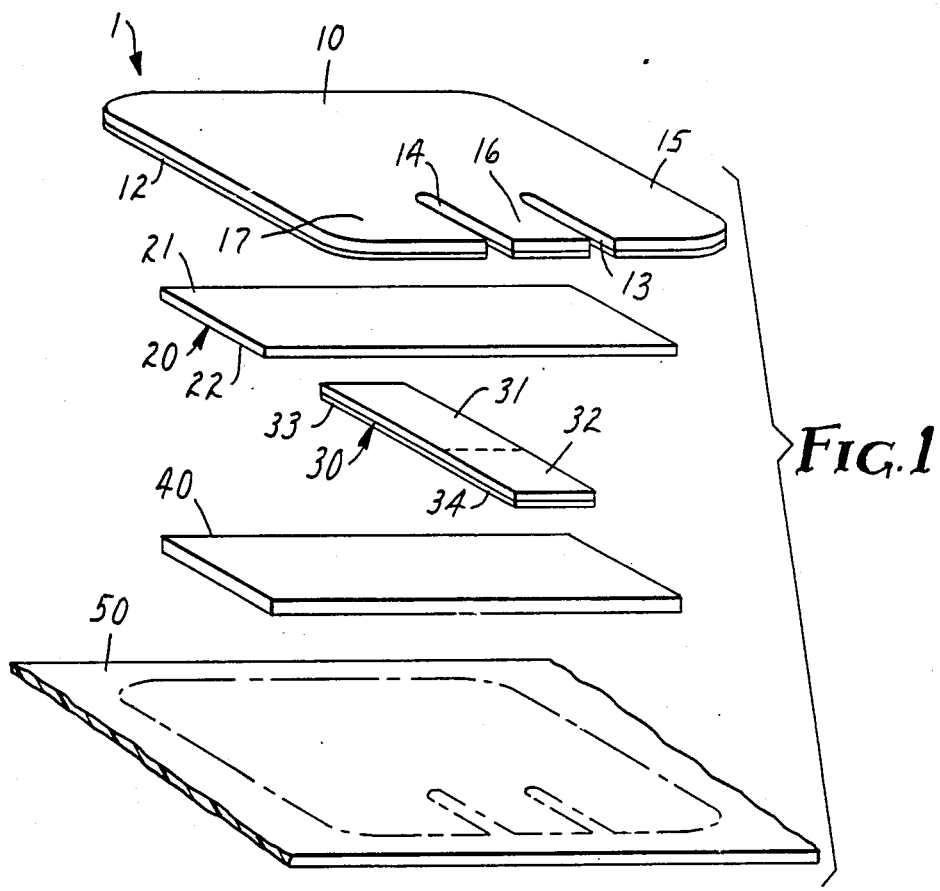
FIG. 1 is an exploded perspective view of a preferred biomedical electrode of this invention.

The elements of a preferred biomedical electrode 1 are shown in FIG. 1. Backing 10 has a continuous coating of biocompatible pressure sensitive adhesive (PSA) 12. The backing 10 and biocompatible PSA 12 are preferably substantially rectangular with cutouts 13 and 14 along one edge. The edge with the cutouts has tabs 15, 16 and 17. Bonding sheet 20 has a first face 21 and second face 22. The surface area of bonding sheet 20 is smaller than that of the backing 10. First face 21 is adhered to the biocompatible PSA 12. Electrical conductor 30 is aligned transverse to the length of the bonding sheet 20. Its top face has a first surface 31 spanning a portion of the second face 22 of the bonding sheet 20 and a second surface 32 adhered to a portion of the biocompatible PSA 12. In the preferred embodiment the electrical conductor 30 is placed so that the second surface 32 bonds to the middle tab 16. The bottom face of electrical conductor 30 is conductive and has a third surface 33 opposing the first surface and a fourth surface 34 opposing the second surface. Electrolyte composition 40 has a surface area no larger than that of the bonding sheet 20 and is adhered to the third surface 33 of the electrical conductor 30 and to a portion of second face 22 of the bonding sheet 20 leaving the fourth surface 34 free of any electrolyte composition. An optional release liner 50 covers the exposed surface of biocompatible PSA 12 and electrolyte composition 40. Such release liners are well known in the art.

Backing 10 may be any material which is conformable to body surfaces and will bond securely to biocompatible PSA 12. Suitable backings include polyethylene foam, vinyl foam, nonwoven cellulose acetate, and spun bonded polyester. A preferred backing is polyethylene foam backing having closed cells which is available from Volteck Inc. (Lawrence Mass.).

The biocompatible PSA 12 may be any of the well known biocompatible pressure sensitive adhesives which provide long term adhesion to skin. Two classes of biocompatible adhesives are acrylate ester copolymers and polyvinyl ethyl ether adhesives. The preferred biocompatible adhesives are copolymers of an iso-octyl acrylate (91% by weight) and N-vinyl pyrrolidone (9% by weight) and are coated 11.5 grains/24 square inches, 48 grams per square meter.

Bonding sheet 20 is selected to be conformable and to adhere to biocompatible PSA 12 and to electrolyte composition 40 more securely than the electrolyte composition adheres to skin. Preferably, after one day a force of at least 200 gm/lineal inch, at a peel angle of 180° is required to separate the bonding sheet from the backing and from the electrolyte material. Suitable materials for use as the bonding sheet include polymeric films, fabrics, nonwoven webs, and paper. The preferred materials for bonding sheet 20 are tissue paper scrims, spun bonded nylons (e.g., stock number 1107-23 available from Monsanto, St. Louis, Mo.) and polyethylene films.

The electrical conductor 30 may be made of any material which conducts electrical signals generated by biomedical events. Electrical conductors generally have at least one surface coated with a conductive metal (for example, tin or silver) or a conductive form of carbon (for example, graphite). Preferably, the electrical conductor is nonpolarizable and meets the standard for Defibrillation Overload Recovery published by the Association for the Advancement of Medical Instruments under the title "American National Standard for Pregelled ECG Disposable Electrodes" and approved by ANSI, Aug. 28, 1984. A particularly preferred electrical conductor 30 is described in commonly assigned application Ser. No. 865,522, filed May 21, 1986. That electrical conductor 30 is a conformable film, e.g., polyester, that has been coated with a primer comprised of a binder and powder particles and thereafter coated with a conductive material. Particularly preferred is lapping film with vapor deposited metallic silver and silver chloride. When assembled with the electrode of the present invention, the preferred electrical conductor has a nonconductive face (surfaces 31 and 32 in FIG. 1) contacting the bonding sheet 20 and biocompatible PSA 12 and a conductive face (surface 33 and 34) a portion of which electrically contacts the electrolyte composition. When the total silver concentration on the conductor does not exceed 15 g/m$^2$, the electrode is X-Ray transluscent.

The electrolyte composition 40 may be conductive gel or an electrically conductive pressure sensitive adhesive (PSA). The preferred electrically conductive PSA is a swellable, dermally non-irritating conformable cohesive, ionic, hydrophilic polymer of the type described in U.S. Pat. Nos. 4,524,087, 4,554,924 and 4,539,996 which are hereby incorporated by reference. The adhesive is derived from an essentially solventless polymerization of a precursor comprised of a water soluble polyhydric alcohol which is liquid at about 20° C., and an ionic unsaturated free radically polymerizable material which is soluble in the polyhydric alcohol. The crosslinking agent is a multifunctional unsaturated free radically polymerizable material. Polymerization is begun with a free radical initiator of either the thermo or photo class. In the preferred electrically conductive adhesive the precursors are acrylic acid (15-20% by weight) and polyacrylic acid (2-4% by weight). The preferred photoinitiator is benzyl dimethyketal 60.1% by weight (available under the tradename Irgacure 651 from Ciba Geigy). The electrolytes plasticizer system is water (5-40% by weight) glycerin 20-60% by weight) and potassium chloride (25-5% by weight).

Figure 2:
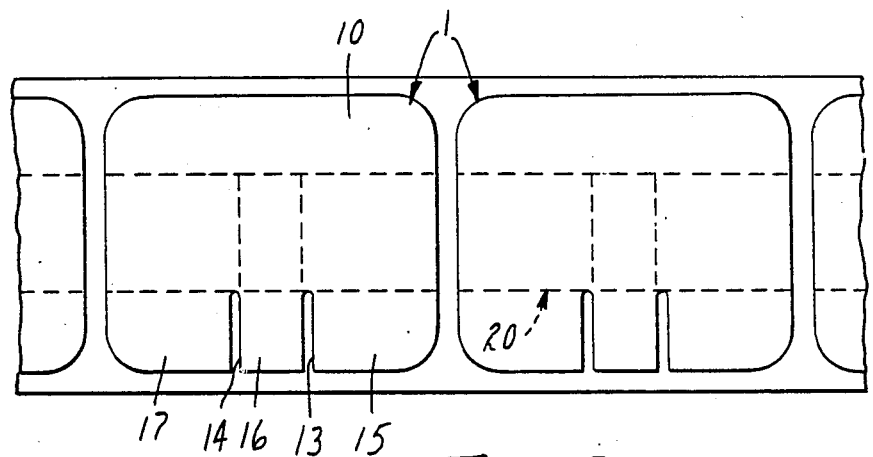
FIG. 2 is a top view of a strip of biomedical electrodes as shown in FIG. 1 when assembled.

FIG. 2 shows a strip of biomedical electrodes 1 assembled on a release liner 50. Bonding sheet 20 shown with phantom lines in FIG. 2, and more clearly shown in FIG. 1, is bonded to the underside of backing 10 by the biocompatible PSA 12 and is aligned with electrolyte composition 40 to provide a compatible bonding base. The bonding sheet 20 and electrolyte composition 40 are positioned centrally with respect to the underside of backing 10.

As shown in FIG. 1, the electrical conductor has a first surface 31 and second surface 32 indicated by dotted lines. First surface 31 spans a portion of the bonding sheet 20. Opposing first surface 31 is third surface 33 which underlies a portion of the electrolyte composition conductive 40. Second surface 32 adheres to the biocompatible PSA 12. Opposing second surface 32 is fourth surface 34 which upon removal from the release liner is exposed and adapted for electrical connection to a lead-wire.

In use, the biomedical electrode of FIGS. 1 and 2 is removed from the release liner and placed on the skin. The electrical conductor is connected to a lead-wire and the lead-wire is connected to an instrument for recording or monitoring electrical signals (e.g., an ECG/EKG machine). Electrical signals generated by biomedical events are transmitted from the skin, through the electrically conductive PSA 40 to the electrical conductor 30 and from the electrical conductor 30 to the lead-wire and recording or monitoring machine. The unique construction of this invention permits use of backing sheets having coatings of biocompatible PSA. An electrolyte composition provides a surface area sufficiently large to detect biomedically generated electrical signals, and the size of the electrical conductor is minimized. The biocompatible PSA allows the electrode to be used for lengthy monitoring and for stress testing. The bonding sheet permits the hydrophilic and hydrophobic compositions to be used in a single electrode. Additionally, when the backing and biocompatible PSA are formed with the preferred tabs extending in a direction transverse to the bonding sheet, and the electrical conductor is adhered to the middle tab, the electrode is not easily dislodged when tension is applied to the lead-wire. This feature is particularly important in stress testing and long term monitoring and other situations where the patient will move or be moved. Surprisingly, the preferred electrode is almost not visible in X-Rays.

An alternative, less preferred, embodiment of the electrode is shown in FIG. 3. In this embodiment, the backing 110 and biocompatible PSA 113 are not formed with cutouts, rather they are formed with extending tab 116 to which the second surface 132 of the electrical conductor 130 is adhered.

FIG. 4 shows another alternative embodiment having no tab adapted for connection to a lead wire. The backing 210 and biocompatible PSA adhesive are formed with projections 250 and 270. The electrical conductor 230 is placed between the projections 250 and 270. The electrolyte composition and bonding sheet 220 are placed remote from the edge so that the second surface 282 of the conductor 230 may adhere to the biocompatible PSA near the edge. This arrangement facilitates attachment of a lead wire to the electrical conductor 230.

Figure 5:
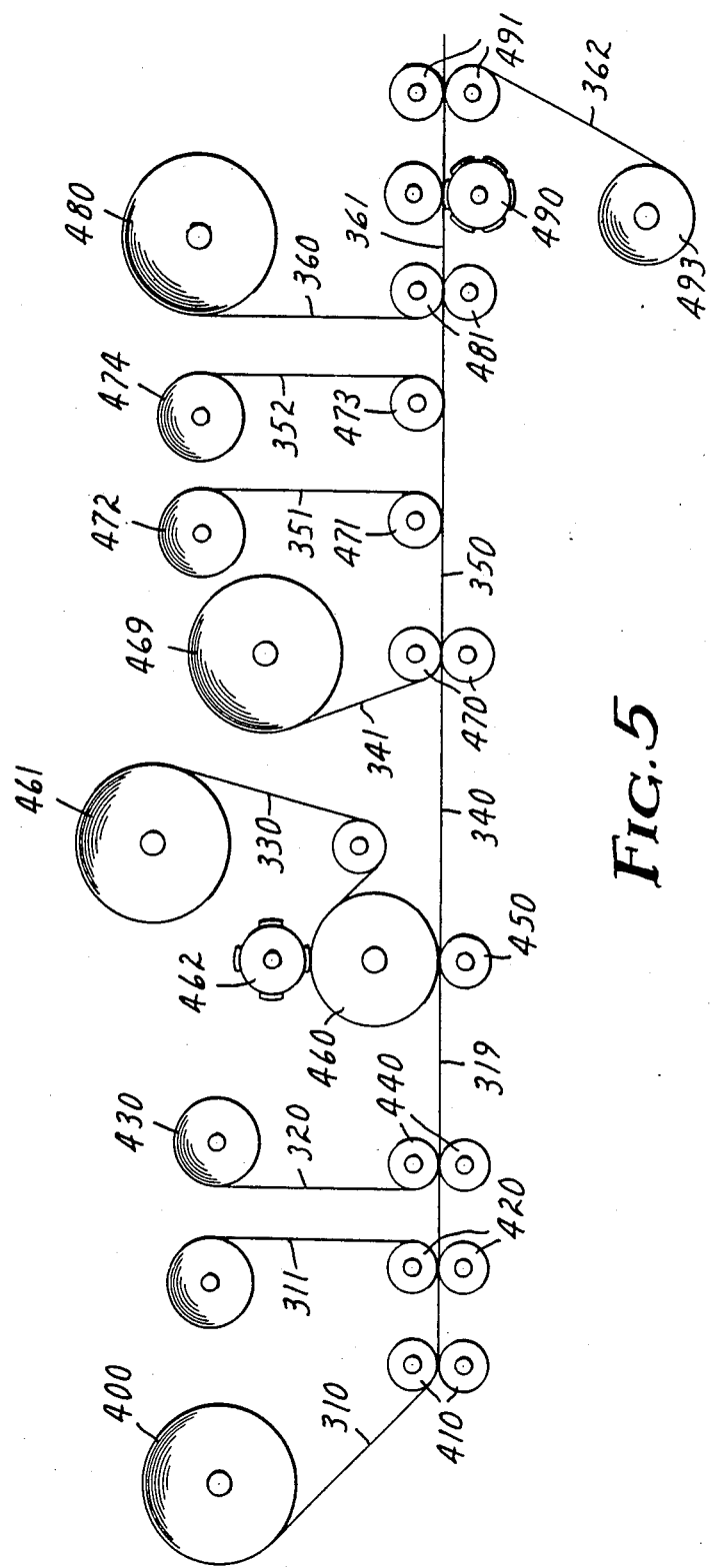
FIG. 5 is a schematic representation of a preferred method of manufacturing biomedical electrodes of this invention.

The preferred method of preparing the biomedical electrode of this invention is shown in FIG. 5. Web 310 is a backing web having one face continuously coated with biocompatible PSA and covered with a larger liner and an edge liner. Backing web 310 is fed from roll 400 through feed rollers 410 to delaminating rollers 420 where the large liner 311 is removed from backing web 310 and taken up on a winding roller 421. Bonding sheet web 320 is fed from roll 430 and laminated to the backing web 310 by rollers 440 whereby two ply laminate 319 is formed. Bonding sheet 320 is narrower than backing web 310 and preferably is positioned centrally with respect to backing web 310.

Two ply laminate 319 proceeds between guide roller 450 and vacuum applicator roller 460 where electrical conductors are applied. The electrical conductors are made by feeding stock conductor material 330 from feed roll 461 to cutter 462. Cutter 462 periodically cuts off a length of conductor material to form an electrical conductor which is carried by vacuum applicator roller 460 until it contacts and adheres to the exposed biocompatible PSA on two ply laminate 319. The feed stock conductor material 330 is wider than the bonding sheet web 320 and narrower than the backing sheet web. The cutter 462 is set to cut off lengths of feed stock conductor material which are shorter than its width. The electrical conductors thus formed are rectangular with their long dimension transverse to the direction of movement of the two ply laminate 319. The electrical conductors are positioned on vacuum applicator roller 460 such that upon engaging two ply laminate 319 a first surface of the electrical conductor spans the bonding sheet 320 and a second surface of the electrical conductor adheres to exposed biocompatible PSA. The composite 340 thus formed proceeds to laminating rollers 470 where electrolyte composition 341 is applied. Electrolyte composition 341 is supplied from stock roll 469 on a carrier web. The electrolyte composition 341 is no wider than the bonding sheet web and is aligned to register with the bonding sheet web. The carrier web 351 is removed by delaminating roller 471 to form composite 350. The delaminated carrier web 351 is taken up on roll 472. The edge liner 352 is delaminated by roller 473 and taken up on roller 474. Release liner 360 is supplied from feed roller 480 and laminated to composite 350 by rollers 481. The composite 361 thus formed includes the backing web with a continuous coating biocompatible adhesive, the bonding sheet web, electrical conductors, electrolyte composition, and a release liner. Die cutting roller 490 cuts this composite 361 to shape, through all layers except the release liner. Weed 362 is removed by rollers 491 and taken up on roller 493.

The foregoing description has been directed to particular preferred embodiments for the purposes of illustration and explanation. Those skilled in the art will appreciate that many modifications and changes will be possible without departing from the scope and spirit of the invention. The following claims are intended to embrace all such modifications and variations.

I claim:

1. A method of manufacturing biomedical electrodes comprising the steps of:
   (a) providing a continuous strip of backing web having a continuous coating of a biocompatible pressure-sensitive adhesive on one surface thereof;
   (b) laminating to the biocompatible pressure-sensitive adhesive coated surface a continuous strip of bonding sheet web which is narrower than the backing web;
   (c) periodically placing electrical conductors at predetermined intervals transversely along the length of the continuous strips of backing and bonding sheet webs such that a first surface of each electrical conductor spans the bonding sheet web and a second surface of each of the electrical conductors adheres to the biocompatible pressure-sensitive adhesive;
   (d) laminating to the composite formed in steps a, b, and c, a continuous strip of an electrolyte composition which electrolyte strip is aligned with the strip of bonding sheet web such that the electrolyte strip overlaps at least a portion of each electrical conductor and contacts the strip of bonding sheet web; and
   (e) die cutting individual electrodes from the composite comprising the strip of backing web, the biocompatible pressure-sensitive adhesive, the strip of bonding sheet web, the electrical conductors, and the electrolyte strip.

2. The method of claim 1 wherein the electrolyte composition is an electrically conductive pressure sensitive adhesive.

3. A method as defined in claim 1 wherein the continuous strip of electrolyte composition in step d is carried by a continuous web of carrier sheet when said electrolyte strip is laminated to the composite formed in steps a, b, and c.

4. A method as defined in claim 3 wherein between steps d and e said continuous web of carrier sheet is removed from the composite formed in steps a, b, c, and d and a release liner is applied to cover the pressure-sensitive adhesive coated surface of each individual electrode.

* * * * *

UNITED STATES PATENT AND TRADEMARK OFFICE
CERTIFICATE OF CORRECTION

PATENT NO. : 4,795,516

DATED : January 3, 1989

INVENTOR(S) : Jerome E. Strand

It is certified that error appears in the above-identified patent and that said Letters Patent is hereby corrected as shown below:

Title page:

Abstract, line 6, "then" should read --than--.

Abstract, line 16, "also," should read --also--.

Col. 8, line 16, & "pressure sensitive" should read
       line 17,    --pressure-sensitive--.

Signed and Sealed this

Twenty-seventh Day of June, 1989

Attest:

DONALD J. QUIGG

Attesting Officer

Commissioner of Patents and Trademarks